United States Patent
Dai et al.

(10) Patent No.: US 11,365,627 B2
(45) Date of Patent: Jun. 21, 2022

(54) METHODS FOR PREDICTING PROPERTIES OF CLEAN FORMATION FLUID USING REAL TIME DOWNHOLE FLUID ANALYSIS OF CONTAMINATED SAMPLES

(71) Applicant: Halliburton Energy Services, Inc., Houston, TX (US)

(72) Inventors: Bin Dai, Spring, TX (US); Christopher Michael Jones, Katy, TX (US); Dingding Chen, Tomball, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 414 days.

(21) Appl. No.: 16/336,172

(22) PCT Filed: Jun. 27, 2018

(86) PCT No.: PCT/US2018/039829
§ 371 (c)(1),
(2) Date: Mar. 25, 2019

(87) PCT Pub. No.: WO2020/005238
PCT Pub. Date: Jan. 2, 2020

(65) Prior Publication Data
US 2021/0054738 A1   Feb. 25, 2021

(51) Int. Cl.
*E21B 47/06* (2012.01)
*E21B 49/08* (2006.01)
(Continued)

(52) U.S. Cl.
CPC ........ *E21B 49/0875* (2020.05); *E21B 49/081* (2013.01); *G01N 21/31* (2013.01);
(Continued)

(58) Field of Classification Search
CPC .. E21B 49/0875; E21B 49/087; E21B 49/081; E21B 47/06
See application file for complete search history.

(56) References Cited

U.S. PATENT DOCUMENTS

| | | | |
|---|---|---|---|
| 8,805,617 B2 * | 8/2014 | Zuo | E21B 49/10 702/11 |
| 9,334,727 B2 * | 5/2016 | Jones | E21B 49/005 |

(Continued)

FOREIGN PATENT DOCUMENTS

WO   2018144606 A1   8/2018

OTHER PUBLICATIONS

PCT Application Serial No. PCT/US2018/039829, International Search Report, dated Feb. 26, 2019, 3 pages.
(Continued)

*Primary Examiner* — Catherine Loikith
(74) *Attorney, Agent, or Firm* — Delizio, Peacock, Lewin & Guerra

(57) ABSTRACT

A method, including disposing a probe of a sensor system in a wellbore to interact with a formation fluid that includes a mud filtrate and a clean fluid that includes one of a formation water, or a formation hydrocarbon fluid including at least one hydrocarbon component. The method includes collecting multiple measurements of a formation fluid from a wellbore, the formation fluid comprising a mud filtrate and a clean fluid, is provided. The clean fluid includes at least one hydrocarbon component, and the method also include identifying a concentration of the mud filtrate and a concentration of the clean fluid in the formation fluid for one of the measurements, and determining at least one hydrocarbon composition and at least one physical property of the clean fluid based on a measurement fingerprint of the hydrocarbon (Continued)

components. A sensor system configured to perform a method as above is also provided.

23 Claims, 10 Drawing Sheets

(51) Int. Cl.
    *G01N 21/31*     (2006.01)
    *G01N 33/28*     (2006.01)
    *E21B 47/07*     (2012.01)

(52) U.S. Cl.
    CPC .......... *G01N 33/2823* (2013.01); *E21B 47/06* (2013.01); *E21B 47/07* (2020.05)

(56) References Cited

U.S. PATENT DOCUMENTS

| | | | |
|---|---|---|---|
| 9,733,389 B2 * | 8/2017 | Hsu | ............... E21B 49/10 |
| 2011/0042070 A1 | 2/2011 | Hsu et al. | |
| 2011/0088949 A1 | 4/2011 | Zuo et al. | |
| 2011/0108720 A1 | 5/2011 | Ford et al. | |
| 2014/0180591 A1 | 6/2014 | Hsu et al. | |
| 2015/0054512 A1 | 2/2015 | Difoggio | |
| 2021/0131951 A1 * | 5/2021 | Dai | ............... G01N 21/31 |

OTHER PUBLICATIONS

PCT Application Serial No. PCT/US2018/039829, International Written Opinion, dated Feb. 26, 2019, 10 pages.

\* cited by examiner

METHODS FOR PREDICTING PROPERTIES OF CLEAN FORMATION FLUID USING REAL TIME DOWNHOLE FLUID ANALYSIS OF CONTAMINATED SAMPLES

BACKGROUND

Field

The exemplary embodiments described herein relate to strategies for hydrocarbon extraction based on measurements performed in a wellbore. More particularly, one or more embodiments disclosed herein relate to methods and systems for determining in real-time the composition and physical properties of clean fluid during fluid extraction in a wellbore.

Background

During downhole formation fluid sampling process, an initial extraction phase typically contains large amounts of contaminants in the extracted fluid, mainly due to the drilling fluid (e.g., "mud filtrate") injected to cool down the drill bit, to balance the high pressure of the wellbore environment, and to remove drilling debris from the wellbore. Accordingly, a clean hydrocarbon sample may not come out of the wellbore until a period of time that may extend for several minutes, an hour, or even longer, depending on the reservoir conditions. Therefore, assessing the quality of the hydrocarbon sample and the convenience of continuing exploitation of a given reservoir may take precious time and resources and increase the exploration cost, until a clean sample comes out of the formation. Adding to this delay, in most applications a detailed sample analysis incudes carrying the sample to a laboratory in an off-site location, which is sometimes remote.

Moreover, commonly found wellbores in the oil and gas production and exploration industry may extend several kilometers underground. Accordingly, many different formation layers and areas are traversed by a wellbore, leading to different types of hydrocarbon liquids extracted along different depths in the wellbore. Therefore, having a precise knowledge of the composition, physical properties and quality of the clean hydrocarbon sample in each of the formation layers and areas of a reservoir is highly beneficial for assessing and assigning production assets and strategies.

BRIEF DESCRIPTION OF THE DRAWINGS

The following figures are included to illustrate certain aspects of the exemplary embodiments described herein, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
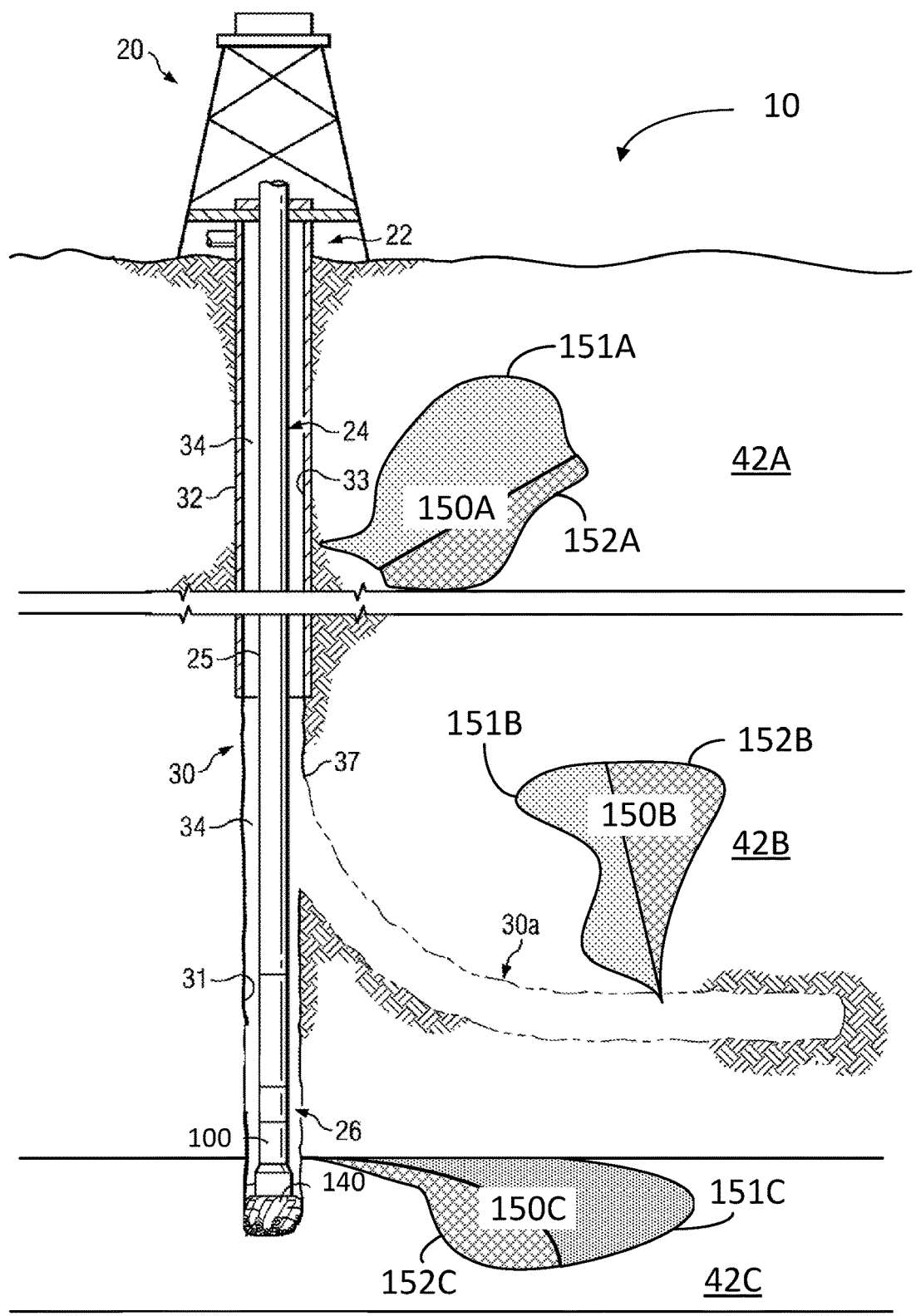
FIG. 1 illustrates a wellbore in a reservoir architecture, according to one or more embodiments.

Understanding of reservoir architecture, particularly reservoir compartmentalization and fluid compositional grading is critical for oil and gas exploration and production activities. Such activities include ensuring drilling safety; identifying and assessing reservoir discovery (e.g., evaluating production potential and value of new reservoirs); optimizing capital investment for production, and designing a field management system across multiple wells. Reservoir fluid analysis (downhole fluid analysis and laboratory fluid analysis), along with conventional wireline and logging-while-drilling (LWD) petro-physical logs, formation pressure testing, and surface mud logs, are applied to understand reservoir complexity. Effective use of laboratory analysis of reservoir fluids typically includes the collection of representative fluids from desired locations through an LWD or wireline sampling operations. It may take weeks to obtain laboratory analysis results back on-site. In some occasions, laboratory analysis may be inconclusive, inaccurate, or simply wrong. When laboratory analysis discovers that the obtained samples are not fit for reservoir evaluation purpose (either non-representative samples or samples from wrong locations), the chance of returning to the site for additional sampling is low. Therefore, operators may have to incur higher risk in production operation and higher uncertainty of asset value assessment without an accurate analysis of the reservoir quality due to the uncertainty (sample quality uncertainty and suboptimal sampling locations) and long delay of reservoir fluid analysis.

Some embodiments determine reservoir architecture in shortened fluid pumping periods, rather than the long pumping periods currently used to obtain a clean sample of the formation fluid, or transporting fluid samples of the formation fluid to a laboratory off-site or at the surface, for analysis. In embodiments consistent with the present disclosure, a short pump-out time provides a sufficiently complete series of sensor measurements of formation fluid-mud filtrate mixtures, each at different reservoir locations. Shortening the pumping time increases the number of locations that may be tested, thus improving measurement resolution along the wellbore without increasing the total logging and measurement time. Methods and systems as disclosed herein are able to provide accurate concentrations of clean formation fluids even when the formation fluid is at least partially (or highly) contaminated with mud filtrate.

In some embodiments, a sensor system consistent with the present disclosure includes multiple sensor channels to leverage a more accurate measurement of downhole fluids during pump-out. In that regard, some embodiments use multivariate statistical, self-resolved techniques to decompose a measurement into physically meaningful concentration profiles and measurement fingerprints of the hydrocarbon components.

In some embodiments, determining a contamination level, e.g., a concentration of the mud filtrate in the formation fluid being extracted at any point in time is desirable for retrieving a clean sample to the surface, for laboratory analysis. This enables substantial reduction in the cost of transportation and laboratory analysis of fluid formation samples (e.g., by substantially reducing return rates of highly contaminated samples from the laboratory site).

FIG. 1 illustrates a wellbore 30 in a reservoir architecture 10, in accordance with some embodiments of the present disclosure. Wellbore 30 cuts through multiple formation layers 42A, 42B, and 42C (hereinafter, collectively referred to as "formation layers 42"), forming a reservoir architecture 10 across different types of geological formations (e.g., formation layers 42). A wellbore 30a may branch out of wellbore 30 at kickoff point 37, forming a more complex structure in reservoir architecture 10, according to one or more embodiments. In each formation layer 42A, 42B, and 42C, an LWD/Wireline tool may encounter a formation fluid 150A, 150B, and 150C (hereinafter, collectively referred to as "formation fluid 150"), respectively. Formation fluid 150 may be at least partially contaminated with mud filtrate 151A, 151B, and 151C, hereinafter, collectively referred to as "mud filtrate 151") at least during an initial measurement phase. In addition, a clean fluid 152A, 152B, and 152C (hereinafter, collectively referred to as "clean fluid 152") may be a true indicator of the formation fluid at formation layers 42A, 42B, and 42C, respectively. To determine the convenience and value of exploiting of reservoir architecture 10, it is desirable to determine the quality and composition of clean fluid 152 for the different formation layers 42.

Various aspects of the present disclosure may be described with respect to drilling rig 20, drill string 24 and sensor system 100. A bottom hole assembly (BHA) 26 may include, in addition to sensor system 100, drill collars, rotary steering tools, directional drilling tools and/or downhole drilling motors. BHA 26 controls drill bit 140 according to wellbore operation parameters such as a rotation speed and the orientation, of drill bit 140. Upon direction from BHA 26, drill string 24 may apply a force on drill bit 140 to form wellbore 30 and wellbore 30a, and to accelerate, stop, or change the direction of drilling of wellbores 30 and 30a.

Wellbore 30 may be defined in part by a casing string 32 extending from a well surface 22 to a selected downhole location. Various types of mud filtrate 151 may be pumped from well surface 22 through drill string 24 to attached rotary drill bit 140. Mud filtrate 151 may be circulated back to well surface 22 through annulus 34 defined in part by outside diameter 25 of drill string 24 and inside diameter 31 of wellbore 30. Inside diameter 31 may also be referred to as the "sidewall" of wellbore 30. Annulus 34 may also be defined by outside diameter 25 of drill string 24 and inside diameter 33 of casing string 32. Mud filtrate 151 may also flow through slots disposed between two adjacent blades on drill bit 140.

Figure 2:
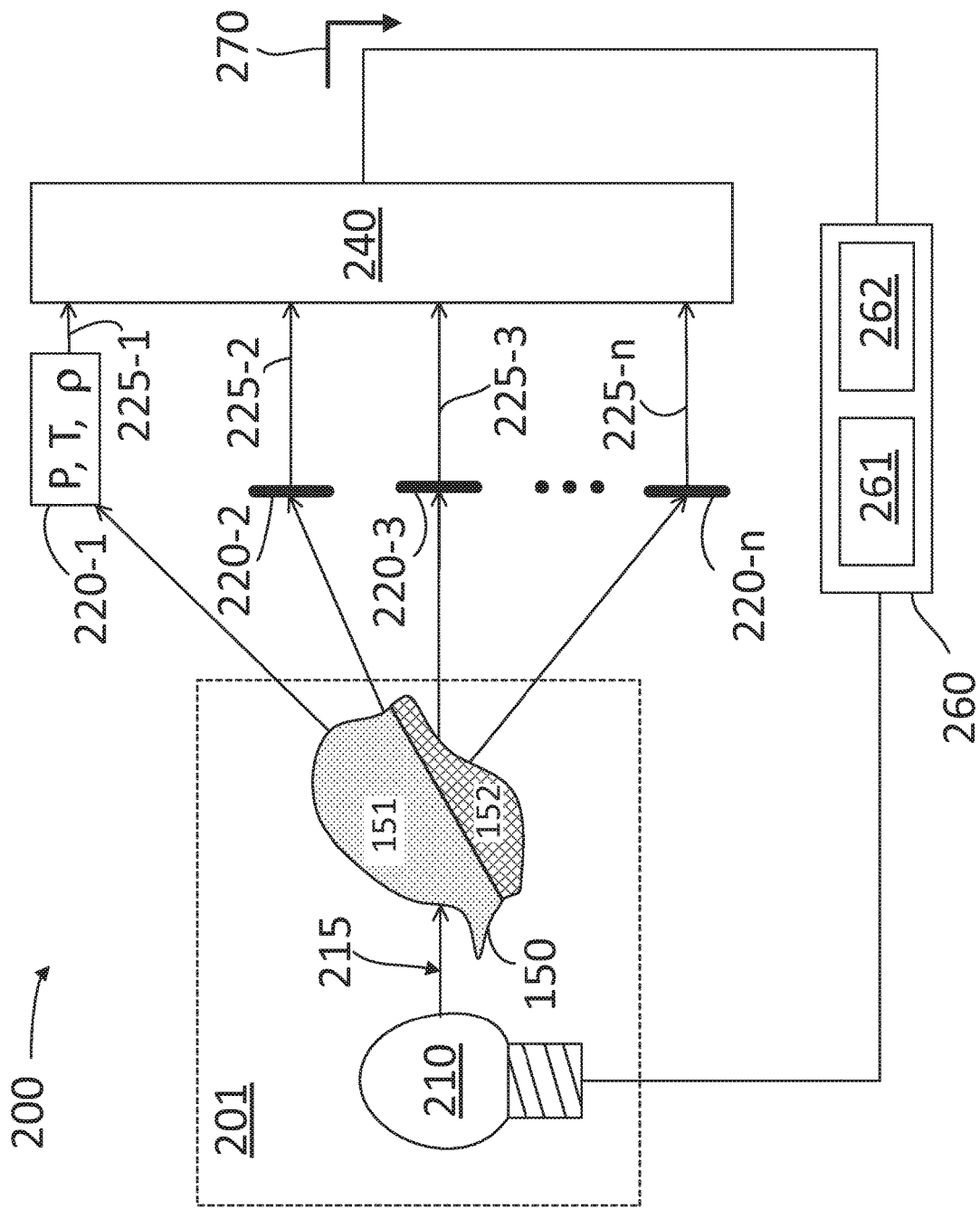
FIG. 2 illustrates a sensor system for collecting real-time data from a formation fluid to determine a clean formation fluid content and a contaminant content in a formation fluid, according to some embodiments.

FIG. 2 illustrates a sensor system 200 for collecting real-time data from a formation fluid to determine a clean formation fluid content and a contaminant content, according to some embodiments. Sensing system 200 includes a probe 201 to couple sensor system 200 with fluid sample 150, which includes a mud filtrate 151 and a clean fluid 152. In some embodiments, probe 201 may include a source 210 that generates a probing signal 215 that interacts with fluid sample 150. For example, in some embodiments source 210 may include an illumination light source, and probing signal 215 may be a light beam. In some embodiments source 210 may be a radioactive source and probing signal 215 may include an alpha particle beam, a beta decay or a gamma ray. Other examples of source 210 may include an acoustic source, a radiofrequency (RF) magnetic resonance source, and the like. Accordingly, probing signal 215 may include sound waves, shear deformation waves, neutron beams, magnetic pulses, spin waves, resistivity, or any combination of the above.

Multiple sensor channels 220-1 through 220-$n$ (hereinafter, collectively referred to as "sensor channels 220") provide signals 225-1 through 225-$n$ (hereinafter, collectively referred to as "signals 225") associated with formation fluid 150. Signals 225 may be associated with fluid properties such as optical properties (e.g., refractive index, absorbance, transmittance, scattering), density ($\rho$), pressure (P), viscosity, capacitance, temperature (T), acoustic properties, bubble point and compressibility. In some embodiments, a density value can be obtained from pressure gradient values determined from pressure signals of the formation fluid. Multiple signals 225 may be collected serially or in parallel, to form a measurement. In that regard, for any given measurement the collection of n signals 225 may be referred to, hereinafter, as a measurement "fingerprint." A transducer 240 converts each of signals 225 into a measurement 270. Transducer 240 may include any electronic device configured to convert an optical signal, a pressure signal, a capacitance signal, and the like, into an electrical signal that may be processed by a controller 260. In that regard, transducer 240 may include a photodetector, an amplifier, a trans-impedance amplifier, an analog-to-digital converter, a digital-to-analog converter, and the like. Controller 260 may include a memory 261, storing instructions, and a processor 262 to execute the instructions and cause sensor system 200 to perform steps in methods consistent with the present disclosure. For example, processor 262 receives measurement 270 and executes the instructions to identify a concentration of the mud filtrate 151 and a concentration of the clean fluid 152 in formation fluid 150, and to determine a hydrocarbon composition of clean fluid 152 based on a measurement fingerprint of the hydrocarbon component.

Processor 262 further executes instructions to cause system 200 to adjust a wellbore operation parameter (such as moving the sampling probe to more optimal locations or additional locations, or adjusting the pumping pressure to optimal level) based on the hydrocarbon composition of clean fluid 152. In some embodiments, sensor channels 220 include optical sensor channels 220-2 through 220-$n$, configured to provide a signal indicative of a spectroscopic characteristic of fluid sample 150, and processor 262 further determines the composition of clean fluid 152 based on the spectroscopic characteristics of selected hydrocarbon components. Sensor channels 220 include at least one of a pressure channel, a temperature channel, or a density channel 220-1 to provide a pressure signal (P), a temperature signal (T), and a density signal ($\rho$), respectively, of the fluid sample. Processor 262 further executes instructions to determine the composition of clean fluid 152 based on at least one of the pressure signal, the temperature signal, or the density signal.

In some embodiments, memory 261 may store instructions and data including a fluid model, wherein the processor is configured to execute the fluid model to determine the hydrocarbon composition of the clean fluid based on the measurement fingerprint of the hydrocarbon component. Memory 261 stores instructions and data that include an equation of state, and processor 262 executes the equation of state to determine the hydrocarbon composition of the clean fluid based on the measurement fingerprint of the hydrocarbon component.

Figure 3:
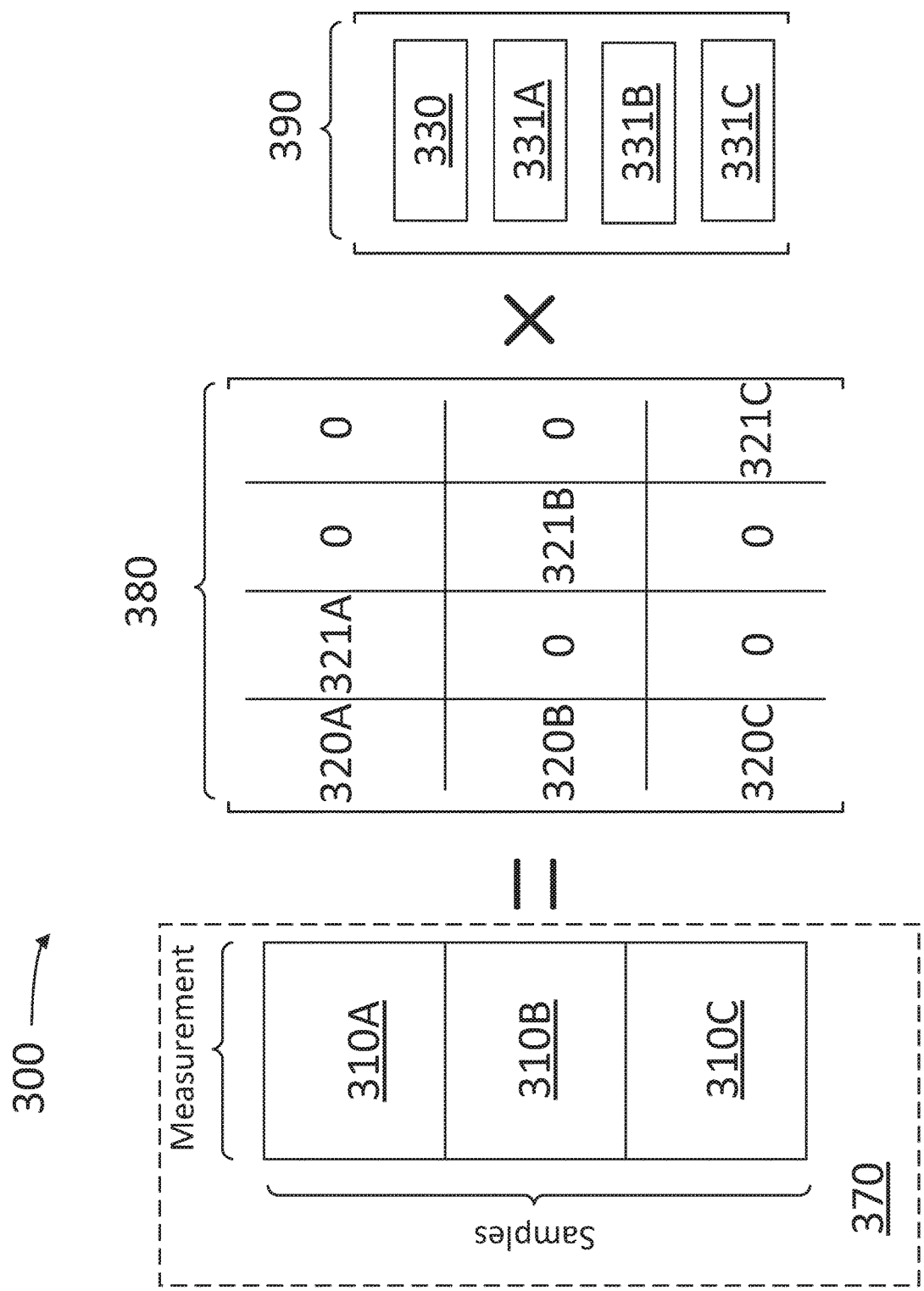
FIG. 3 illustrates a multivariate clean fluid resolving decomposition to determine a clean formation fluid content and a contaminant content, according to some embodiments.

FIG. 3 illustrates a multivariate clean fluid resolving matrix decomposition 300 to determine a clean formation fluid content and a contaminant content in a formation fluid, according to some embodiments. Accordingly, LWD and wireline formation sensor systems may be equipped with multiple sensor channels providing signals to form a measurement (e.g., sensor channels 220, signals 225 and measurement 270) for real-time analysis of formation fluids (e.g., formation fluid 150). A number, M, of measurements may be collected by sensor system 200 while pumping the formation fluid for a period of time (e.g., 60 minutes pump-outs) during three pump-out operations at different depths in the wellbore (e.g., formation layers 42A, 42B, and 42C, cf. FIG. 1). Accordingly, a matrix D 370 may be obtained wherein the M rows in each of blocks 310A, 310B, and 310C have n components from the sensor channel signals for each measurement over formation layers A, B, and C, respectively. A statistical multivariate clean fluid resolving method as disclosed herein estimates hydrocarbon concentration, contamination level and clean fluid properties by assuming that measurement matrix 370 (D) may be linearly decomposed as the product of a concentrations matrix 380 (C) and a fingerprint matrix 390 (S).

The columns of C matrix 380 include concentration levels of the mud filtrate and the concentration levels of clean fluids for each of the formation layers A, B, and C. For example, column 320A in C matrix 380 includes M elements indicative of the mud filtrate concentration for each of the M measurements performed at formation layer A. Likewise, column 320B in C matrix 380 includes M elements indicative of the mud filtrate concentration for each of the M measurements performed at formation layer B. And column 320C in C matrix 380 includes M elements indicative of the mud filtrate concentration for each of the M measurements in formation layer C. Columns 320A, 320B and 320C will be hereinafter collectively referred to as "column 320," having 3M elements indicative of the mud filtrate concentration for all measurements across the three formation layers A, B, and C. In turn, column 321A includes M elements indicative of the concentration of a first identified clean fluid in formation layer A. Column 321A includes M elements indicative of the concentration of a second identified clean fluid in formation layer B. Column 321C includes M elements indicative of the concentration of a third identified clean fluid in formation layer C. Columns 321A, 321B and 321C will be referred to, hereinafter, as "clean fluid concentration columns 321."

Next to columns 320A and 321A, two columns of M zeroes each indicate that no presence of the second and third identified clean fluids is expected in formation layer A, by construction of C matrix 380. Likewise, two columns of M zeroes each, next to columns 320B and 321B, indicate that no presence of the first and third identified clean fluids is expected in formation layer B. Similarly, two columns of M zeroes each, next to columns 320C and 321C, indicate that no presence of the first and second identified clean fluids is expected in formation layer C. Moreover, it is expected that the sum of an element in column 320 with a corresponding element (in the same row of C matrix 380) of clean fluid columns 321 be equal, or approximately equal, to one (=1, or totaling %100 of the sample formation fluid).

The rows of S matrix 390 include the measurement fingerprints of the mud filtrate and the clean fluid for each of the formation layers. For example, row 330 may include n values for the expected signals from the sensor system 200 when formation fluid 150 includes the mud filtrate only (cf. FIG. 2). Row 331A in S matrix 390 may include n values for the expected signals from sensor system 200 when formation fluid 150 includes the first clean fluid only (e.g., the clean formation fluid of formation layer A). Row 331B in S matrix 390 may include n values for the expected signals from sensor system 200 when formation fluid 150 includes the second clean fluid only (e.g., the clean formation fluid of formation layer B). And row 331C in S matrix 390 may include n values for the expected signals from sensor system 200 when formation fluid 150 includes the third clean fluid only (e.g., the clean formation fluid of formation layer C). Rows 331A, 331B and 331C will be collectively referred to, hereinafter, as "clean fluid fingerprints 331." Thus, embodiments as disclosed herein enable fast data processing of measurement matrix 370 to determine a concentration of mud filtrate of the formation fluid (e.g., column 320) and of clean fluids (e.g., "clean fluid columns 321") from C matrix 380. Additionally, methods as disclosed herein determine the measurement fingerprint of clean fluids of mixtures from a formation fluid (e.g., clean fluid fingerprints 331).

A statistical multivariate clean fluid resolving method as disclosed herein decomposes D matrix 370 as follows:

$$D = C \cdot S^T + E; \quad (1)$$

Where E is an error matrix (e.g., including systematic and stochastic error, such as sensor error, and interaction nonlinearities).

Eq. 1 has an infinite number of solutions for C matrix 380 and S matrix 390, given a D matrix 370. For example, given matrices C and S that satisfy Eq. 1, new matrices C' and S' will also satisfy Eq. 1 when $C'=C \cdot R$, $S'=S \cdot R$, and R is any 4×4 transformation matrix including a 4-dimensional rotation and an arbitrary scaling factor $$R \cdot R^T = R \cdot R^{-1} = 1;$$

$$\Rightarrow D = C \cdot R \cdot R^{-1} \cdot S^T + E; \quad (2)$$

Accordingly, the solutions to Eq. 1 may be constrained by including further properties of concentration values and of measurement fingerprints. For example, concentration values (C matrix 380) and measurement fingerprints (S matrix 390) include nonnegative values (e.g., nonnegative signal fingerprints and nonnegative concentrations of endmembers). Also, the summation of concentrations of two or more components (e.g., volume fraction, and the like) is equal, or approximately equal, to 100%, (e.g., closure constrain on the rows of C matrix 380). In some embodiments, a density measurement or a priori knowledge of drilling fluid filtrate density may further constrain the summation over the rows of C matrix 380. In some embodiments, optical sensing signals of clean fluids are used to include further constrains on the values of C matrix 380.

In addition to the constraints applied to Eq. 1, methods as disclosed herein include an alternating iteration process to solve Eq. 1. An alternating iteration consistent with embodiments disclosed herein starts with an initial estimate of either the columns in C matrix 380 or the rows in S matrix 390. Assuming for instance, an initial estimate of the rows of S matrix 390, a residual error $E_C$ is minimized by adjusting the values of C matrix 380 so that $$E_C = \arg \min \|D_{PCA} - C \cdot S_T\|; \quad (3)$$

In some embodiments, the new estimate of C matrix 380 is fixed and used in a new step that includes estimating a new matrix, S, to minimize a residual error, $E_S$, according to $$E_S = \arg \min \|D_{PCA} - C \cdot S^T\|; \quad (4)$$

When a new matrix S is determined, and fixed in equation 3 to determine a new matrix, C, Eq. 3 and Eq. 4 iterate alternately, until the residual error ($E_S = E_C$) converges.

In some embodiments, an a-priori knowledge of both mud filtrate and formation fluid properties can be incorporated into the constrained alternating least squares algorithm (e.g., as known measurement fingerprints 330 or 331 in S matrix 390) to obtain accurate results.

While the above example includes multiple measurements for three formation layers A, B, C, any number of formation layers can be included, without limitation. Formation layers A, B and C may correspond to different depths along a wellbore, or different reservoir compartments, or even different reservoirs. In fact, some embodiments may use measurements from a formation layer. Augmenting the size of D matrix 370 to include additional formation layers in the method increases by M×m the number of components in Eq. 1, while the number of variables increases only by n+2 (the signal values for the measurement fingerprint of the clean fluid, the mud filtrate concentration, and the clean fluid concentration in the new formation layer). Accordingly, an augmented multivariate analysis as illustrated in matrix decomposition 300 provides information for a reservoir architecture, and also enhances the precision of the determination of the clean fluid concentration and the clean fluid measurement fingerprint.

Figure 4:
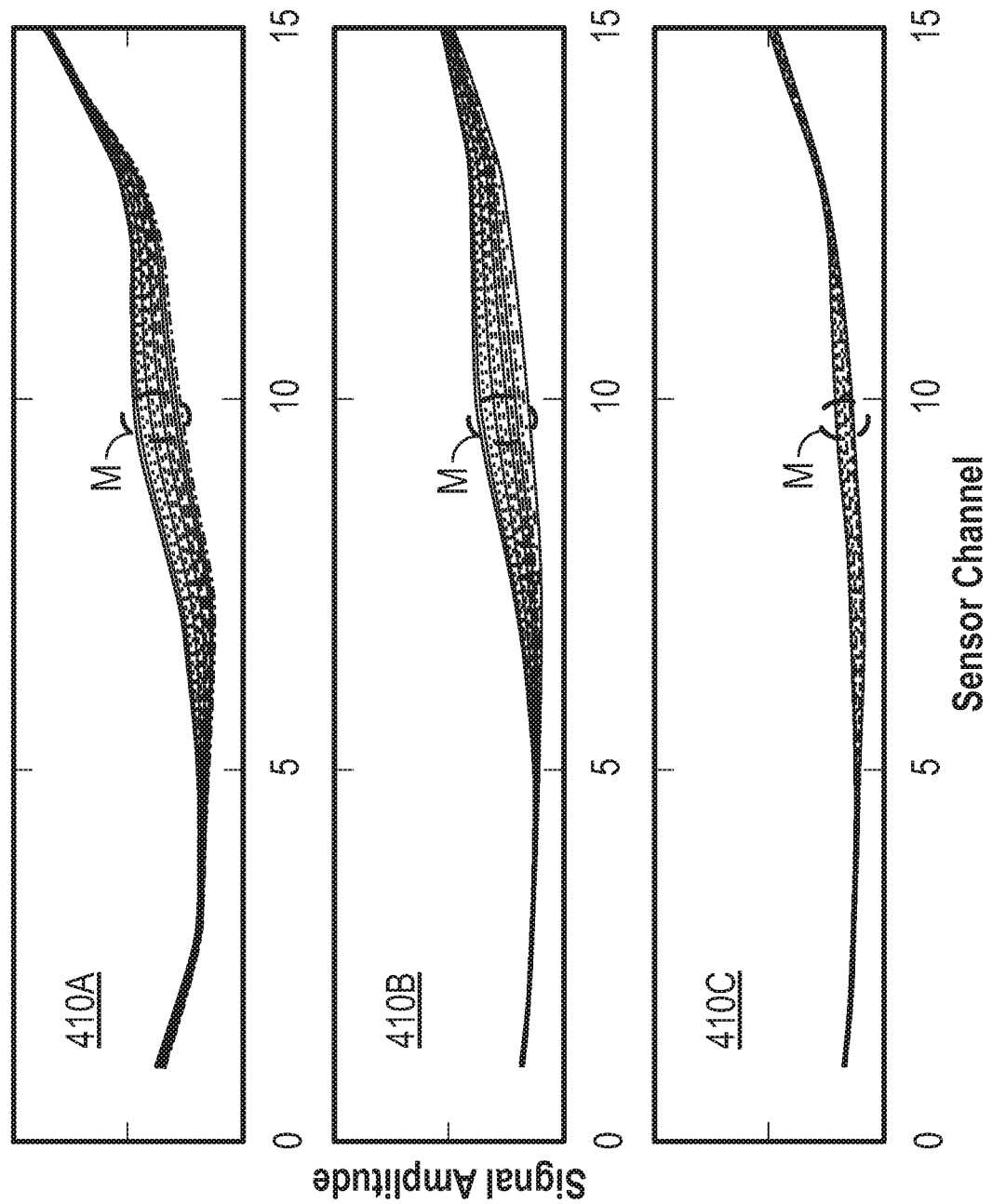
FIG. 4 illustrates multiple sensor readings from three pump-out regions in a wellbore, according to some embodiments.

FIG. 4 illustrates multiple sensor readings 410A, 410B and 410C from three pump-out regions in the wellbore (e.g., formation layers 42A, 42B and 42C, cf. FIG. 1), according to some embodiments. For example, sensor readings 410A may include signals associated with the fluid sample in formation layer A. Accordingly, sensor readings 410A form M rows of length n in the first block of D matrix 370. Sensor readings 410B may include signals associated with the fluid sample in formation layer B (e.g., M rows of length n in the second block of D matrix 370). Sensor readings 410C may include signals associated with the fluid sample in formation layer B (e.g., M rows of length n in the third block of D matrix 370).

Figure 5:
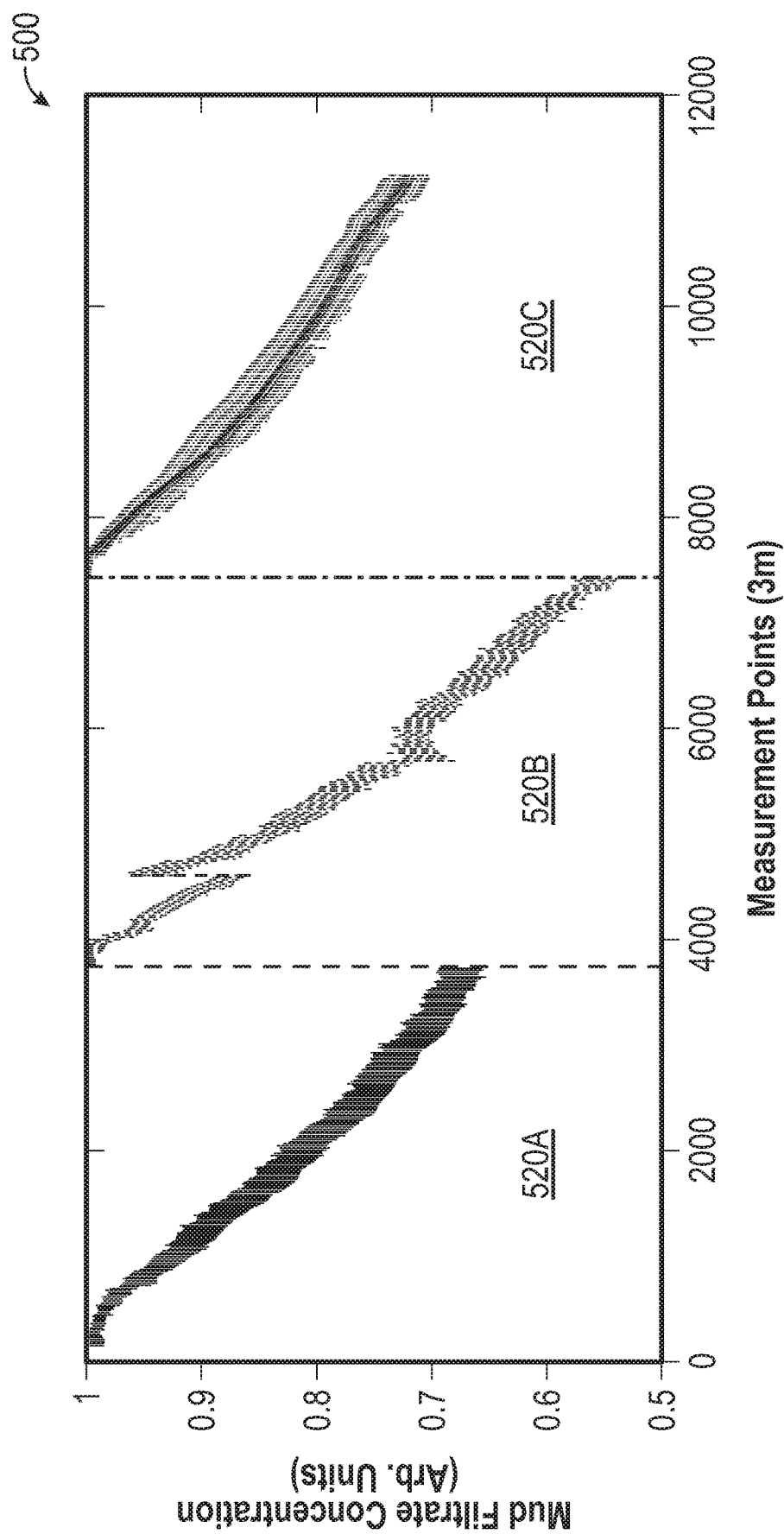
FIG. 5 illustrates a mud-filtrate contamination level (in volume fraction) for the three pump-out regions in FIG. 4, according to some embodiments.

FIG. 5 illustrates mud-filtrate contamination levels 500 (e.g., in volume fraction) for the three formation layers in FIGS. 1, 3-4, according to some embodiments. An alternating constrained least squares optimization as described in FIG. 3 is used to decompose D matrix 370 and obtain concentration profiles 520A, 520B, and 520C (hereinafter, collectively referred to as "concentration profiles 520") corresponding to the mud filtrate concentration 500 in each of formation layers A, B, and C, respectively (e.g., column 320, cf. FIG. 3). Each of concentration profiles 520 includes M data points collected over a measurement period for each formation layer (e.g., 60 minutes). Accordingly, embodiments as disclosed herein provide valuable, real-time information about formation fluid contamination and how this is changing in time, as the pumping progresses. With this information, an operator may be able to estimate the time it will take to achieve a desired purity in the formation fluid at a given pumping rate. Therefore, the operator may decide to increase, decrease, or stop the pumping rate to move on to a different formation layer, a different compartment within the reservoir, or to a new reservoir altogether. Moreover, by accurately determining composition even when the formation fluid is still highly contaminated (e.g., early in a pump-out process), an operator may obtain also an accurate measurement fingerprint of the clean formation fluid (e.g., through the row of S matrix 390).

Figure 6:
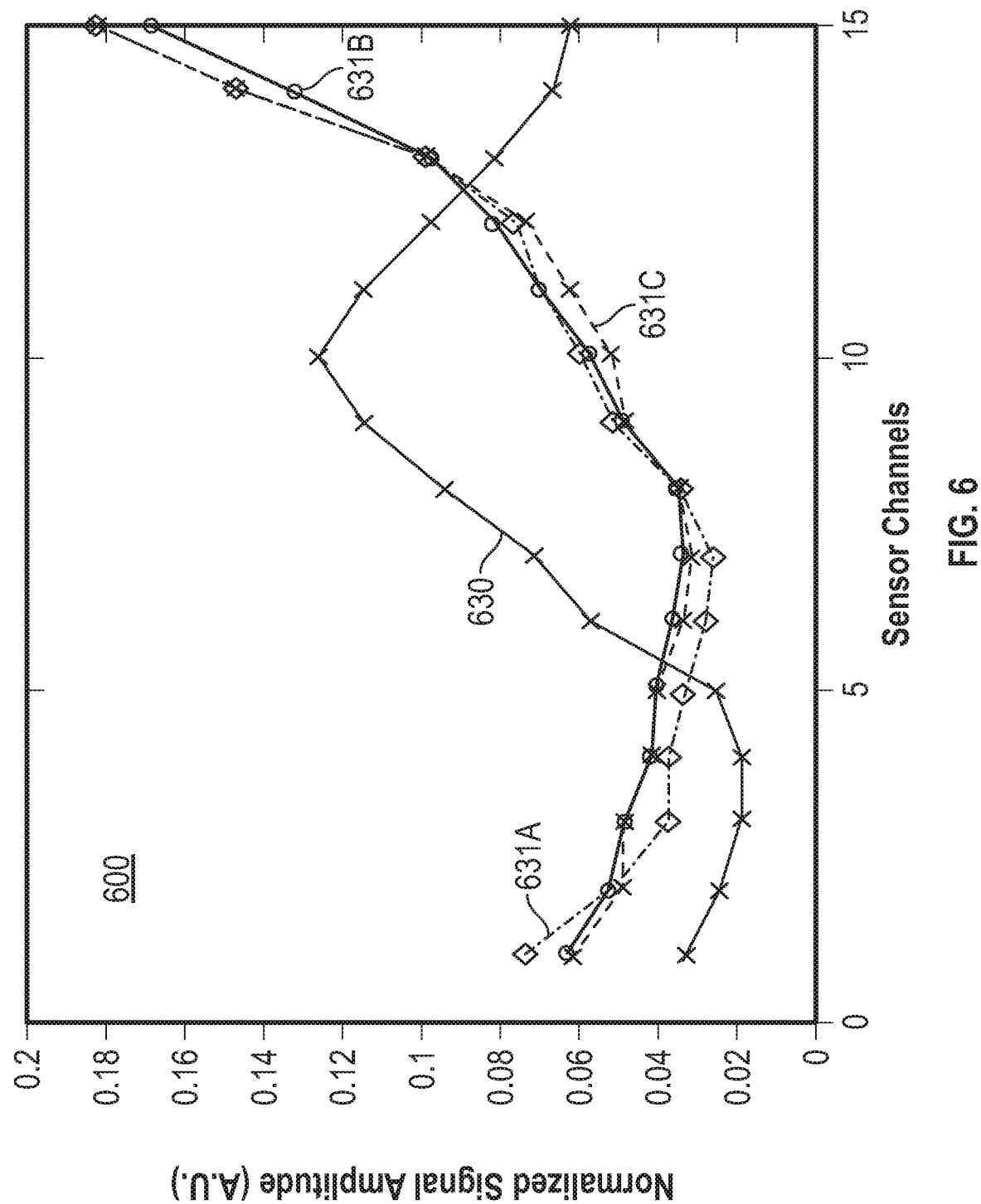
FIG. 6 illustrates measurement fingerprints of mud-filtrate and clean formation fluids from the different pump-out regions in FIG. 4, according to some embodiments.

FIG. 6 illustrates chart 600 with measurement fingerprints of mud-filtrate 630 and of clean formation fluids 631A, 631B, and 631C (hereinafter, collectively referred to as "measurement fingerprints 631"), from the different formation layers in FIGS. 1, and 3-4), according to some embodiments. Accordingly, measurement fingerprints 630 and 631 are graphical representations of the rows of S matrix 390 (e.g., measurement fingerprints 330 and 331, cf. FIG. 3). In some embodiments, measurement fingerprints 631, which indicate the properties of the pure formation fluid (e.g., formation fluid 152, c. FIGS. 1 and 2) may be obtained at an early stage of the pump-out process in each formation layer (e.g., A, B or C). Accordingly, methods and systems as disclosed herein save rig operation time by significantly reducing the pump-out time without the need to retrieve fluid samples form the reservoir and transport to the laboratory for thorough analysis.

Measurement fingerprints 630 and 631 (e.g., normalized sensor responses are used) may be used in the analysis of a reservoir architecture (e.g., reservoir architecture 10. (f FIG. 1). In some embodiments, a multivariate calibration model may be applied to each of measurement fingerprints 631 to predict the compositional information of the formation fluid at each formation layer. For example, some embodiments may include linear calibration models such as multi-linear regression (MLR), ridge regression (RR), principal component regression (PCR), partial least squares (PLS) regression, least absolute shrinkage and selection operator (LASSO) regression, or any combination of the above. Some embodiments may include nonlinear calibration models such as artificial neural networks (ANN), support vector machine (SVM) analysis, Gaussian process regression (GPR) and any combination of the above. For example, each of measurement fingerprints 631 may include different concentration of a hydrocarbon component, e.g., methane (C1), ethane (C2), propane (C3), tetra- or penta-carbon components (C45, including n-butane, isobutane, pentane, isopentane, and neopentane), carbon dioxide ($CO_2$), saturates, aromatics, resins, and asphaltenes, and the like. A number of multivariate clustering techniques, including nearest neighbor, soft independent modelling of class analogy (SIMCA), and the like, or simple trending analysis, can be applied to either compositional data (e.g., concentration profiles 520, cf. FIG. 5) or measurement fingerprints 631 to conduct fluid comparison, reservoir fluid grading and reservoir compartmentalization.

In some embodiments, an equation of state (EOS) analysis or empirical PVT composition correlation of measurement fingerprints 631 provides the ability to obtain PVT parameters (density, phase envelope, viscosity, bubble point, compressibility, and the like). PVT parameters are valuable for understanding the reservoir architecture, for reservoir value appraisal, and to establish a field development plan largely reducing the amount of fluid samples to retrieve for laboratory PVT analysis. In some embodiments, EOS results enable an operator to apply a constraint on reservoir architecture and compositional grading.

Figure 7:
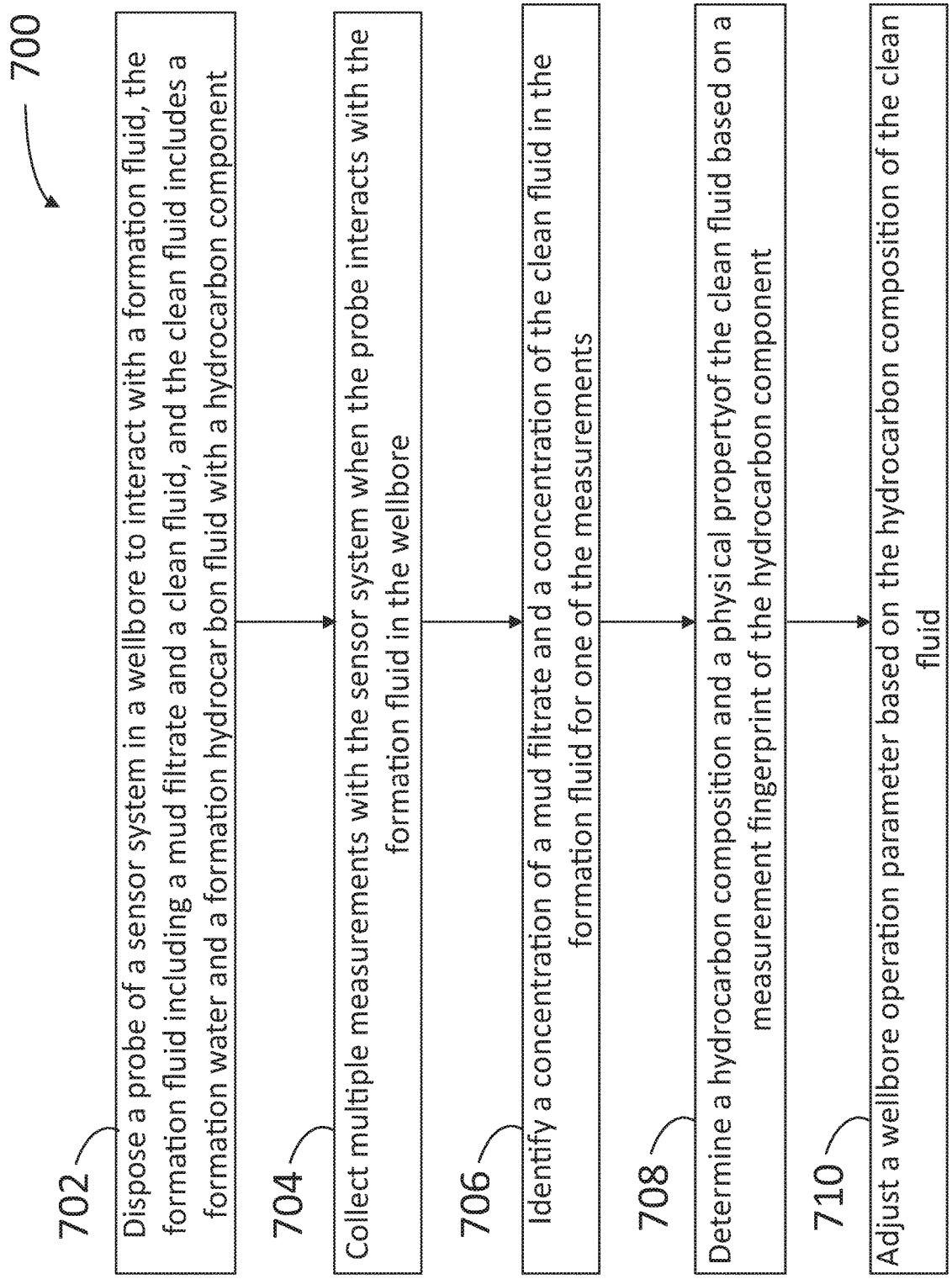
FIG. 7 illustrates a flow chart including steps in a method for determining the components of a clean formation fluid, according to some embodiments.

FIG. 7 illustrates a flow chart including steps in a method 700 for determining the components of a clean formation fluid, according to some embodiments. The clean formation fluid may be an end member of a formation fluid including a mud filtrate in a wellbore for oil and gas extraction (e.g., wellbores 30 and 818, formation fluid 150, mud filtrate 151, and clean fluid 152, cf. FIGS. 1, 8 and 9). Embodiments consistent with method 700 include operating a sensor system (e.g., sensor systems 100 and 200, cf. FIG. 2). Accordingly, a sensor system in methods consistent with method 700 may include a probe and multiple sensing channels, a transducer, and a controller (e.g., probe 201, sensing channels 220, transducer 240, and controller 260, cf. FIG. 2). In some instances, at least one or more of the steps in method 700 is performed by a computer including a memory circuit storing commands executed by a processor circuit (e.g., controller 260, memory 261, processor 262, cf. FIG. 2). Steps in methods consistent with the present disclosure may include at least any of the steps in method 700, performed in any order. Furthermore, embodiments consistent with the present disclosure may include one or more of the steps in method 700 performed overlapping in time, or simultaneous in time.

Step 702 includes disposing the probe of the sensor system in the wellbore to interact with the formation fluid. The formation fluid may include a mud filtrate and a clean fluid, wherein the clean fluid may include a formation water and a formation hydrocarbon fluid that includes at least one hydrocarbon component.

Step 704 includes collecting multiple measurements with the sensor system when the probe interacts with the formation fluid in the wellbore. In some embodiments, step 704 includes collecting a first plurality of measurements at a first depth in the wellbore, and collecting a second plurality of measurements at a second depth in the wellbore, further comprising determining a first quality of the clean fluid at the first depth in the wellbore and a second quality of the clean fluid at the second depth in the wellbore. In some embodiments, step 704 includes collecting measurements until a convergence criterion is met for the concentration of the mud filtrate, the concentration in the clean fluid of the hydrocarbon component, and a linear model for the measurement. In some embodiments, step 704 includes collecting an optical measurement from the formation fluid, the optical measurement indicative of a spectroscopic characteristic of the hydrocarbon component.

In some embodiments, step 704 includes collecting a first plurality of measurements at a first depth in the wellbore, and collecting a second plurality of measurements at a second depth in the wellbore, further comprising determining a first quality of the clean fluid at the first depth in the wellbore and a second quality of the clean fluid at the second depth in the wellbore. In some embodiments, step 704 includes collecting measurements until a convergence criterion is met for the concentration of the mud filtrate, the concentration in the clean fluid of the hydrocarbon component, and a linear model for the measurement. In some embodiments, step 704 includes collecting an optical measurement from the formation fluid, the optical measurement indicative of a spectroscopic characteristic of the hydrocarbon component.

Step 706 includes identifying a concentration of a mud filtrate and a concentration of the clean fluid in the formation fluid for at least one of the measurements. In some embodiments, step 706 includes forming a linear relation between the concentration of the mud filtrate and the concentration of the clean fluid in the formation fluid with a plurality of sensor channel values in the measurement. In some embodiments, step 706 includes selecting the concentration of the mud filtrate and the concentration of the clean fluid in the formation fluid based on a measurement for the formation fluid. In some embodiments, step 706 includes selecting a measurement for the formation fluid based on the concentration of the mud filtrate and the concentration of the clean fluid in the formation fluid. In some embodiments, step 706 includes finding an equation of state for the formation fluid based on at least one of a pressure measurement, a temperature measurement, and a density measurement.

In some embodiments, step 706 includes forming a linear relation between the concentration of the mud filtrate and the concentration of the clean fluid in the formation fluid with a plurality of sensor channel values in the measurement. In some embodiments, step 706 includes selecting the concentration of the mud filtrate and the concentration of the clean fluid in the formation fluid based on a measurement for the formation fluid. In some embodiments, step 706 includes selecting a measurement for the formation fluid based on the concentration of the mud filtrate and the concentration of the clean fluid in the formation fluid. In some embodiments, step 706 includes finding an equation of state for the formation fluid based on at least one of a pressure measurement, a temperature measurement, and a density measurement.

Step 708 includes determining a hydrocarbon composition of the clean fluid based on a measurement fingerprint of the hydrocarbon component. In some embodiments, step 708 also includes determining at least one physical property of the clean fluid, such as a density, a bubble point, and a viscosity. In some embodiments, step 708 includes evaluating a fluid model for the clean fluid using the hydrocarbon concentration. Step 708 may be performed in-situ, without the need for retrieving formation fluid from the downhole. The reservoir architecture determination service allow reservoir fluids been analyzed at multiple locations in the wellbore without having to collect samples (e.g., extract a formation fluid sample to the surface or to an off-site location). Accordingly, high-resolution fluid architecture determination will significantly reduce uncertainty of reservoir structure and fluid understanding, including reservoir compartmentalization and reservoir fluid grading study to improve understanding of the reservoir architecture. In some embodiments, step 708 includes evaluating a fluid model for the clean fluid using the concentration of the hydrocarbon component.

Step 710 includes adjusting a wellbore operation parameter based on the composition of the clean fluid. In some embodiments, step 710 includes extracting the formation fluid from a selected depth in the wellbore based on the wellbore operation parameter.

Figure 8:
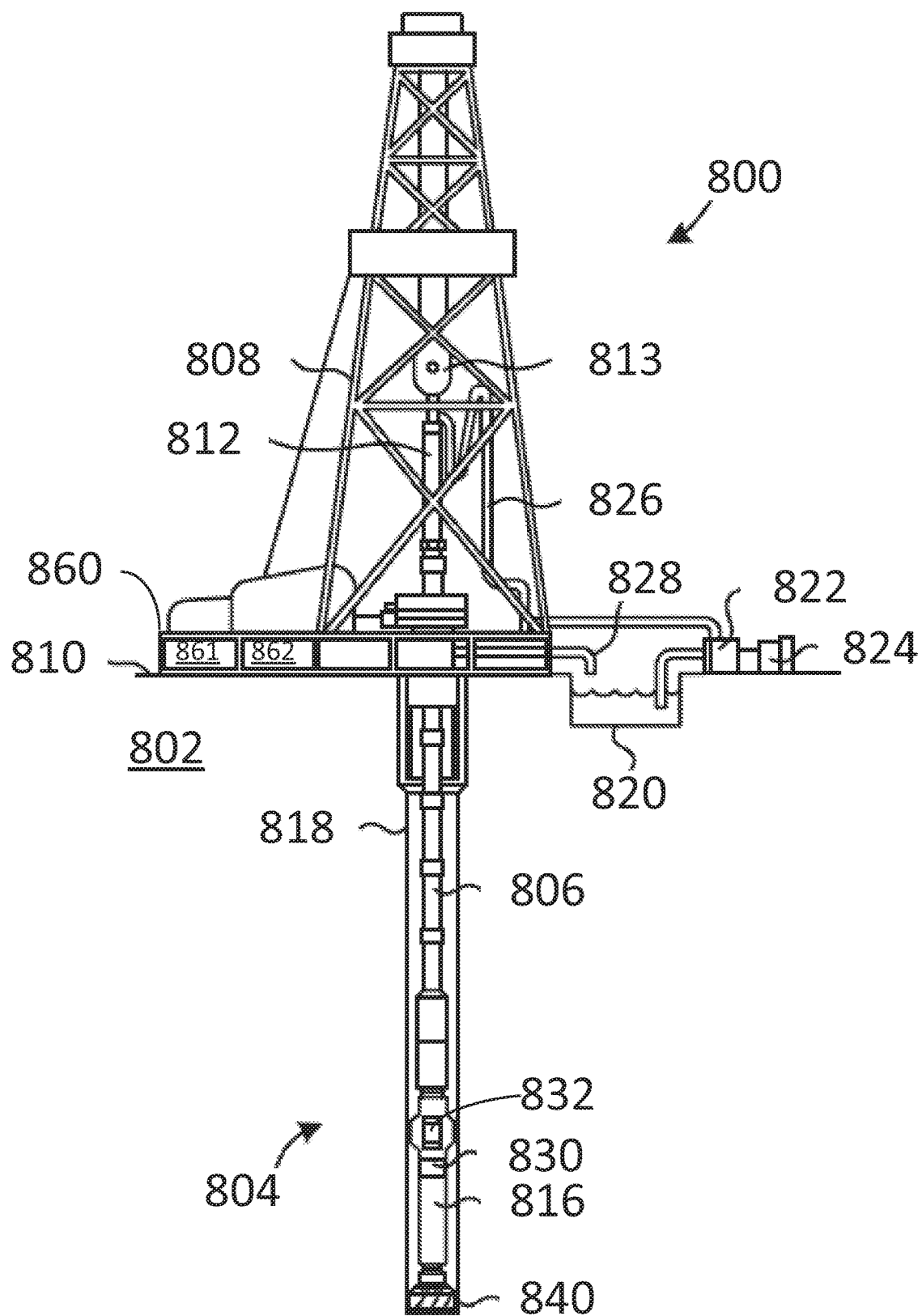
FIG. 8 illustrates a drilling system configured with a downhole tool having a sensor system to measure a formation fluid in measurement-while-drilling (MWD) and a logging-while-drilling (LWD) operations.

FIG. 8 illustrates a drilling system 800 configured with at least one tool having a sensor system 832 (e.g., sensor systems 100 and 200) in a measurement-while-drilling (MWD) or logging-while-drilling (LWD) operation. A wellbore 818 may be created by drilling into the earth 802 using drilling system 800. Drilling system 800 may be configured to drive a BHA 804 positioned or otherwise arranged at the bottom of a drill string 806 extended into the earth 802 from a derrick 808 arranged at the surface 810. The derrick 808 includes a Kelly 812 and a traveling block 813 used to lower and raise the Kelly 812 and the drill string 806.

BHA 804 may include a drill tool 840 operatively coupled to a tool string 816 which may be moved axially within a drilled wellbore 818 as attached to the tool string 816. During operation, drill tool 840 penetrates the earth 802 and thereby creates wellbore 818. BHA 804 provides directional control of drill tool 840 as it advances into earth 802. Tool string 816 can be mounted with various measurement tools (not shown) such as, but not limited to, measurement-while-drilling (MWD) and logging-while-drilling (LWD) tools, that may be configured to take downhole measurements of drilling conditions. In other embodiments, the measurement tools may be self-contained within drill string 806, as shown in FIG. 8.

Fluid or "drilling fluid" from a mud tank 820 may be pumped downhole using a mud pump 822 powered by an adjacent power source, such as a prime mover or motor 824. The drilling fluid may be pumped from mud tank 820, through a stand pipe 826, which feeds the drilling fluid into drill string 806 and conveys the same to drill tool 840. The drilling fluid exits one or more nozzles arranged in drill tool 840 and in the process cools drill tool 840. After exiting drill tool 840, the mud circulates back to the surface 810 via the annulus defined between the wellbore 818 and the drill string 806, and in the process, returns drill cuttings and debris to the surface. Some of the drilling fluid contaminates the formation fluid as mud filtrate, especially during the early stages of extraction. The cuttings and mud mixture are passed through a flow line 828 and are processed such that a cleaned mud is returned down hole through the stand pipe 826 once again.

BHA 804 may further include a downhole tool 830. For this embodiment, downhole tool 830 includes sensor system 832 configured with multiple sensor channels (e.g., sensor systems 100 and 200, and sensor channels 220). Downhole tool 830 may be positioned between drill string 806 and drill tool 840.

A controller 860 including a memory 861 and a processor 862 can be communicatively coupled to sensor system 832 of downhole tool 830. While sensor system 832 may be placed near the bottom of wellbore 818, and extend for a few inches above drill tool 840, a communication channel may be established by using electrical signals or mud pulse telemetry for most of the length of tool string 806 from drill tool 840 to controller 860. In certain embodiments, sensor system 832 can obtain real time measurements of an amount of a clean formation fluid, and real time measurements of an amount of a contaminant in the clean formation fluid (e.g., mud filtrate 151). In addition, drilling system 800 can be configured with one or more additional tools to obtain real time property measurements of a fluid comprising a formation fluid downhole.

Memory 861 includes commands which, when executed by processor 862 cause controller 860 to perform steps in methods consistent with the present disclosure. More specifically, controller 860 may provide commands to and receive data from sensor system 832 during operation. For example, in some embodiments, controller 860 may receive information from sensor system 832 about drilling conditions in wellbore 818 and controller 860 may provide a command to BHA 804 to modify certain drilling parameters. For example, controller 860 may provide a command to adjust or change the drilling direction of drill tool 840 based on a message contained in information provided by sensor system 832. In that regard, the information provided by sensor system 832 to controller 860 may include certain drilling conditions, such as physical or chemical properties of the formation fluid in the subterranean environment. More generally, sensor system 832 may provide data such as gas-oil-ratio (GOR) content, a methane concentration, a $CO_2$ concentration, or a hydrocarbon content of the formation fluid in the wellbore. Accordingly, controller 860 may use processor 862 to determine a characteristic of the sample in a medium surrounding drill tool 840 using the data collected from the sensor system 832.

Figure 9:
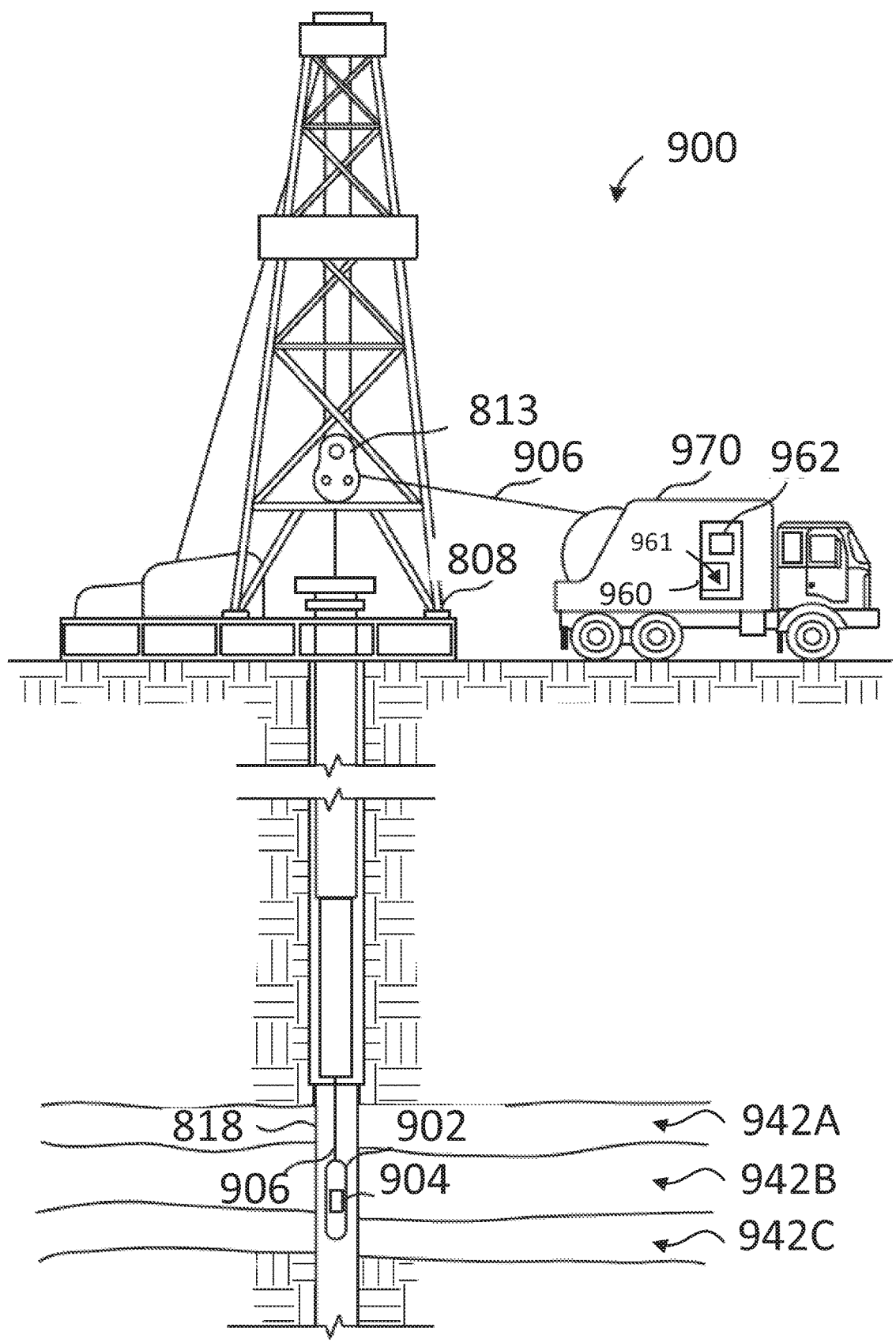
FIG. 9 illustrates a wireline system configured with a downhole tool having a sensor system to measure a formation fluid during formation testing and sampling.

FIG. 9 illustrates a wireline system 900 configured with a tool having a sensor system 904 (e.g., sensor systems 100 and 200) during formation testing and sampling. The formation may include a reservoir architecture having formation layers 942A, 942B, and 942C (e.g., formation layers 42, and A, B, and C, cf. FIGS. 1 and 3). After drilling of wellbore 818 is complete, it may be desirable to know more details of types of formation fluids and the associated characteristics through sampling with use of wireline formation tester. System 900 may include a wireline tool 902 that forms part of a wireline logging operation that can include one or more of sensor system 904 as described herein (e.g., optical computing device or sensor systems 100, 200 or 832). System 900 may include derrick 808 supporting traveling block 813. Wireline tool 902, such as a probe or sonde, may be lowered by wireline or logging cable 906 into wellbore 818. Wireline tool 902 may be lowered to the bottom of the region of interest and subsequently pulled upward at a substantially constant speed by wireline or logging cable 906. Wireline tool 902 may be configured to measure fluid properties of the wellbore fluids, and a measurement generated by wireline tool 902 and its associated sensor system 904 can be communicated to a surface logging facility 970 for storage, processing, and/or analysis. The sensor system 904 may include one or more optical computing devices with ICEs specifically designed according to the spectral fingerprint of selected hydrocarbon components. Logging facility 970 may be provided with electronic equipment 960, including one or more processors 961 and one or more memory 962 for various types of signal processing. Memory 962 may store instructions and commands which, when executed by processor 961, can provide determinations and fluid characterization as disclosed herein.

Figure 10:
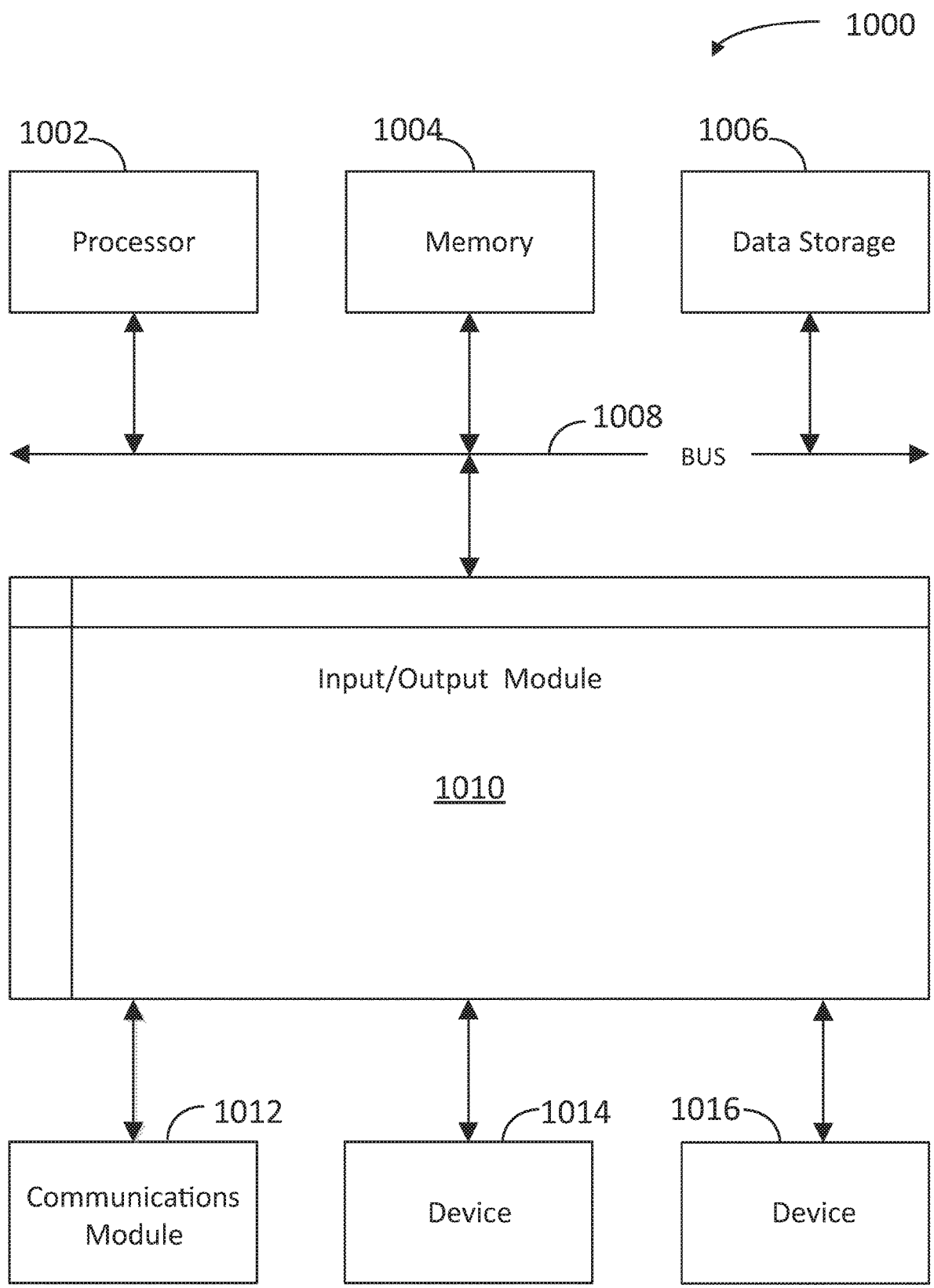
FIG. 10 is a block diagram illustrating an example computer system 1000 with which the methods of FIG. 7 can be implemented.

FIG. 10 is a block diagram illustrating an example computer system 1000 with which the method of FIG. 7 can be implemented. In certain aspects, computer system 1000 may be implemented using hardware or a combination of software and hardware, either in a dedicated server, or integrated into another entity, or distributed across multiple entities.

Computer system 1000 includes a bus 1008 or other communication mechanism for communicating information, and a processor 1002 coupled with bus 1008 for processing information. By way of example, the computer system 1000 may be implemented with one or more processors 1002. Processor 1002 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 1000 can include, in addition to hardware, code that creates an execution environment for the computer program in question, e.g., code that constitutes processor firmware, a protocol stack, a database management system, an operating system, or a combination of one or more of them stored in an included memory 1004, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 1008 for storing information and instructions to be executed by processor

1002. The processor 1002 and the memory 1004 can be supplemented by, or incorporated in, special purpose logic circuitry.

The instructions may be stored in the memory 1004 and implemented in one or more computer program products, i.e., one or more modules of computer program instructions encoded on a computer readable medium for execution by, or to control the operation of, the computer system 1000, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP. Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, and xml-based languages. Memory 1004 may also be used for storing temporary variable or other intermediate information during execution of instructions to be executed by processor 1002.

A computer program as discussed herein does not necessarily correspond to a file in a file system. A program can be stored in a portion of a file that holds other programs or data (e.g., one or more scripts stored in a markup language document), in a file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 1000 further includes a data storage device 1006 such as a magnetic disk or optical disk, coupled to bus 1008 for storing information and instructions. Computer system 1000 may be coupled via input/output module 1010 to various devices. Input/output module 1010 can be any input/output module. Exemplary input/output modules 1010 include data ports such as USB ports. The input/output module 1010 is configured to connect to a communications module 1012. Exemplary communications modules 1012 include networking interface cards, such as Ethernet cards and modems. In certain aspects, input/output module 1010 is configured to connect to one or more devices, such as an input device 1014 and/or an output device 1016. Exemplary input devices 1014 include a keyboard and a pointing device, e.g., a mouse or a trackball, by which a user can provide input to the computer system 1000. Other kinds of input devices 1014 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Exemplary output devices 1016 include display devices, such as a LCD (liquid crystal display) monitor, for displaying information to the user.

According to one aspect of the present disclosure, method 700 can be implemented using a computer system 1000 in response to processor 1002 executing one or more sequences of one or more instructions contained in memory 1004. Such instructions may be read into memory 1004 from another machine-readable medium, such as data storage device 1006. Execution of the sequences of instructions contained in main memory 1004 causes processor 1002 to perform the process steps described herein. One or more processors in a multi-processing arrangement may also be employed to execute the sequences of instructions contained in memory 1004. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component. e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication network can include, for example, any one or more of a LAN, a WAN, the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computer system 1000 can include clients and servers. A client and server are generally remote from each other and typically interact through a communication network. The relationship of client and server arises by virtue of computer programs running on the respective computers and having a client-server relationship to each other. Computer system 1000 can be, for example, and without limitation, a desktop computer, laptop computer, or tablet computer. Computer system 1000 can also be embedded in another device, for example, and without limitation, a mobile telephone, a PDA, a mobile audio player, a Global Positioning System (GPS) receiver, a video game console, and/or a television set top box.

The term "machine-readable storage medium" or "computer-readable medium" as used herein refers to any medium or media that participates in providing instructions to processor 1002 for execution. Such a medium may take many forms, including, but not limited to, non-volatile media, volatile media, and transmission media. Non-volatile media include, for example, optical or magnetic disks, such as data storage device 1006. Volatile media include dynamic memory, such as memory 1004. Transmission media include coaxial cables, copper wire, and fiber optics, including the wires that include bus 1008. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter affecting a machine-readable propagated signal, or a combination of one or more of them.

Embodiments disclosed herein include:

A. A method, including disposing a probe of a sensor system in a wellbore to interact with a formation fluid. The formation fluid includes a mud filtrate and a clean fluid, and the clean fluid includes one of a formation water or a formation hydrocarbon fluid including at least one hydrocarbon component. The method also includes collecting multiple measurements with the sensor system when the probe interacts with the formation fluid in the wellbore, identifying a concentration of the mud filtrate and a concentration of the clean fluid in the formation fluid for one of the measurements, and determining at least one hydrocarbon composition and at least one physical property of the clean fluid based on a measurement fingerprint of the hydrocarbon component.

B. A system, including a probe to interact with a fluid sample in a wellbore, the fluid sample comprising a mud filtrate and a clean fluid. The clean fluid includes a hydrocarbon component. The system also includes multiple sensor channels, each sensor channel configured to provide a signal associated with the fluid sample, a transducer configured to convert the signal from each of the multiple sensor channels into a measurement, a memory, storing instructions, and a processor, configured to receive the measurement. The processor is also configured to execute the instructions to identify a concentration of the mud filtrate and a concentration of the clean fluid in the fluid sample for the measurement, and to determine at least one hydrocarbon composition and at least one physical property of the clean fluid based on a measurement fingerprint of the hydrocarbon component.

C. A non-transitory, computer-readable medium storing instructions which, when executed by a processor, cause a computer to perform a method. The method includes disposing a probe of a sensor system in a wellbore to interact with a formation fluid. The formation fluid includes a mud filtrate and a clean fluid, and the clean fluid includes a hydrocarbon component. The method also includes collecting multiple measurements with the sensor system when the probe interacts with the formation fluid in the wellbore and identifying a concentration of the mud filtrate and a concentration of the clean fluid in the formation fluid for one of the measurements. The method also includes determining at least one hydrocarbon composition and at least one physical property of the clean fluid based on a measurement fingerprint of the hydrocarbon component, and adjusting a wellbore operation parameter based on the hydrocarbon composition of the clean fluid to extract the formation fluid from a selected depth in the wellbore based on the wellbore operation parameter.

Each of embodiments A, B, and C may have one or more of the following additional elements in any combination. Element 1, further including adjusting a wellbore operation parameter based on the hydrocarbon composition and the physical property of the clean fluid, and extracting the formation fluid from a selected depth in the wellbore based on the wellbore operation parameter. Element 2, wherein collecting multiple measurements with the sensor system includes collecting a first plurality of measurements at a first depth in the wellbore, and collecting a second plurality of measurements at a second depth in the wellbore, further including determining a first quality of the clean fluid at the first depth in the wellbore and a second quality of the clean fluid at the second depth in the wellbore. Element 3, wherein collecting multiple measurements with the sensor system includes collecting measurements until a convergence criterion is met for the concentration of the mud filtrate and the concentration of the clean fluid in a linear model for the measurement. Element 4, wherein collecting multiple measurements with the sensor system includes collecting an optical measurement from the formation fluid, the optical measurement indicative of a spectroscopic characteristic of the hydrocarbon component. Element 5, wherein identifying a concentration of a mud filtrate and a concentration of the clean fluid in the formation fluid includes forming a linear relation between the concentration of the mud filtrate and the concentration of the clean fluid with a plurality of sensor channel values in the measurement. Element 6, wherein identifying a concentration of a mud filtrate and a concentration of the clean fluid in the formation fluid includes selecting the concentration of the mud filtrate and the concentration of the clean fluid in the formation fluid based on a measurement for the formation fluid. Element 7, wherein identifying a concentration of a mud filtrate and a concentration of the clean fluid in the formation fluid includes selecting a measurement for the formation fluid based on the concentration of the mud filtrate and the concentration of the clean fluid in the formation fluid. Element 8, wherein the physical property of the clean fluid includes one of a density, a bubble point, and a viscosity, and identifying a concentration of a mud filtrate and a concentration of the clean fluid in the formation fluid includes finding an equation of state for the formation fluid based on the physical property of the clean fluid. Element 9, wherein determining a hydrocarbon composition of the clean fluid based on the measurement fingerprint of the hydrocarbon component includes determining a reservoir fluid architecture based on the hydrocarbon composition and a physical property of the clean fluid at multiple locations in the wellbore. Element 10, wherein determining a hydrocarbon composition of the clean fluid based on the measurement fingerprint of the hydrocarbon component includes evaluating a fluid model for the clean fluid using the measurement fingerprint of the hydrocarbon component.

Element 11, wherein the processor further executes instructions to cause the system to adjust a wellbore operation parameter based on the hydrocarbon composition of the clean fluid. Element 12, wherein the sensor channels include an optical sensor channel configured to provide a signal indicative of a spectroscopic characteristic of the fluid sample, and the processor further executes instructions to determine the hydrocarbon composition of the clean fluid based on the spectroscopic characteristic of the fluid sample. Element 13, wherein the sensor channels include at least one of a pressure channel, a temperature channel, or a density channel configured to provide a pressure signal, a temperature signal, and a density signal, respectively, of the fluid sample, and the processor further executes instructions to determine the hydrocarbon composition of the clean fluid based on at least one of the pressure signal, the temperature signal, or the density signal. Element 14, wherein the memory stores instructions and data that include a fluid model, and wherein the processor is configured to execute the fluid model to determine the hydrocarbon composition of the clean fluid based on the measurement fingerprint of the hydrocarbon component. Element 15, wherein to determine a hydrocarbon composition of the clean fluid based on the measurement fingerprint of the hydrocarbon component the processor executes instructions to determine a reservoir fluid architecture based on the hydrocarbon composition of the clean fluid at multiple locations in a wellbore. Element 16, wherein the memory stores instructions and data that include an equation of state, and wherein the processor is configured to execute the equation of state to determine the hydrocarbon composition of the clean fluid based on the measurement fingerprint of the hydrocarbon component.

Element 17, wherein collecting multiple measurements with the sensor system includes collecting a first plurality of measurements at a first depth in the wellbore, and collecting a second plurality of measurements at a second depth in the wellbore, further including determining a first quality of the clean fluid at the first depth in the wellbore and a second quality of the clean fluid at the second depth in the wellbore. Element 18, wherein determining a hydrocarbon composition of the clean fluid based on the measurement fingerprint of the hydrocarbon component includes determining a reservoir fluid architecture based on the hydrocarbon composition of the clean fluid at multiple locations in the wellbore. Element 19, wherein collecting multiple measurements of a formation fluid from a wellbore includes collecting an optical measurement from the formation fluid, the optical measurement indicative of a spectroscopic characteristic of the hydrocarbon component. Element 20, wherein collecting multiple measurements of a formation fluid from a wellbore includes collecting at least one of a pressure measurement, a temperature measurement, and a density measurement from the formation fluid.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMs, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM, and flash EPROM.

The exemplary embodiments described herein is well adapted to attain the ends and advantages mentioned as well as those that are inherent therein. The particular embodiments disclosed above are illustrative only, as the exemplary embodiments described herein may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. Embodiments as disclosed herein may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, ranges of values (of the form, "from about a to about b," or, equivalently, "from approximately a to b," or, equivalently, "from approximately a-b") disclosed herein are to be understood to set forth every number and range encompassed within the broader range of values. Also, the terms in the claims have their plain, ordinary meaning unless otherwise explicitly and clearly defined by the patentee.

Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (e.g., each item). The phrase "at least one of" does not exclude selection of more than one item; rather, the phrase allows a meaning that includes at least one of any one of the items, and/or at least one of any combination of the items, and/or at least one of each of the items. By way of example, the phrases "at least one of X, Y, and Z" or "at least one of X, Y, or Z" each refer to only X, only Y, or only Z; any combination of X, Y, and Z; and/or at least one of each of X, Y, and Z.

What is claimed is:

1. A method, comprising:
   disposing a probe of a sensor system in a wellbore to interact with a formation fluid;
   collecting multiple measurements with the sensor system when the probe interacts with the formation fluid in the wellbore across formation depths;
   decomposing the multiple measurements into a plurality of contamination levels and a plurality of measurement fingerprints;
   for a first of the formation depths,
      identifying a first subset of the plurality of contamination levels corresponding to the first formation depth as contamination levels of mud filtrate and a second subset of the plurality of contamination levels corresponding to the first formation depth as contamination levels of clean fluid in the formation fluid; and
      determining at least one hydrocarbon composition and at least one physical property of the clean fluid with a multivariate model based, at least in part, on a first of the plurality of measurement fingerprints that corresponds to the first formation depth.

2. The method of claim 1, further comprising adjusting a wellbore operation parameter based on the hydrocarbon composition and the physical property of the clean fluid for the first formation depth and extracting the formation fluid from the first formation depth in the wellbore based on the wellbore operation parameter.

3. The method of claim 1, wherein collecting multiple measurements with the sensor system comprises collecting a first plurality of measurements at the first formation depth in the wellbore, and collecting a second plurality of measurements at a second formation depth in the wellbore, further comprising identifying a third subset of the plurality of contamination levels corresponding to the second formation depth as contamination levels of the clean fluid at the second formation depth in the wellbore.

4. The method of claim 1, wherein collecting multiple measurements with the sensor system comprises collecting measurements until a convergence criterion is met for the contamination levels of mud filtrate and the contamination levels of clean fluid in a linear model for the measurements.

5. The method of claim 1, wherein collecting multiple measurements with the sensor system comprises collecting an optical measurement from the formation fluid, the optical measurement indicative of a spectroscopic characteristic of the hydrocarbon component.

6. The method of claim 1, wherein identifying the first subset of contamination levels as the contamination levels of mud filtrate at the first formation depth and a second subset of contamination levels as contamination levels of clean fluid at the first formation depth comprises forming a linear relation between the contamination levels of mud filtrate and the contamination levels of clean fluid with a plurality of sensor channel values in the measurements.

7. The method of claim 1, wherein the physical property of the clean fluid comprises one of a density, a bubble point, and a viscosity, and identifying the contamination levels of mud filtrate and contamination levels of clean fluid in the formation fluid at the first formation depth comprises finding an equation of state for the formation fluid based on the physical property of the clean fluid.

8. The method of claim 1, further comprising determining a reservoir fluid architecture based on the hydrocarbon composition and the at least one physical property of the clean fluid at multiple of the formation depths in the wellbore.

9. The method of claim 1, wherein decomposing the multiple measurements comprises iteratively minimizing residual error of the plurality of contamination levels and of the plurality of measurement fingerprints until a convergence criterion is met.

10. The method of claim 1, wherein decomposing the multiple measurements is according to a constrained alternating least squares algorithm.

11. The method of claim 10, wherein the constrained alternating least squares algorithm comprises constraints that include at least one of a nonnegative measurement fingerprint value, a nonnegative contamination level value, a closure constraint between the plurality of contamination levels of the fluid sample, and a density measurement of mud filtrate.

12. The method of claim 1, wherein the multivariate model comprises a linear model or a nonlinear model.

13. A system, comprising:
   a probe to interact with a fluid sample;
   multiple sensor channels, each sensor channel configured to provide a signal associated with the fluid sample;
   a transducer configured to convert the signal from each of the multiple sensor channels into a measurement;
   a memory storing instructions; and
   a processor, configured to receive measurements and execute the instructions to:
   decompose measurements from different formation depths into a plurality of contamination levels and a plurality of measurement fingerprints;
   for each of the different formation depths,
      identify a first subset of the plurality of contamination levels as contamination levels of mud filtrate and a second subset of the plurality of contamination levels as contamination levels of clean fluid in the fluid sample at the formation depth; and
      determine a hydrocarbon composition and at least one physical property of the clean fluid with a multivariate model based, at least in part, on a first of the plurality of measurement fingerprints corresponding to the formation depth.

14. The system of claim 13, wherein the memory further has stored thereon instructions to cause the system to adjust a wellbore operation parameter based on the hydrocarbon composition of the clean fluid.

15. The system of claim 13, wherein the sensor channels comprise an optical sensor channel configured to provide a signal indicative of a spectroscopic characteristic of the fluid sample, wherein the instructions to determine the hydrocarbon composition of the clean fluid comprise instructions executable by the processor to cause the system to determine the hydrocarbon composition of the clean fluid based on the spectroscopic characteristic of the fluid sample.

16. The system of claim 13, wherein the sensor channels comprise at least one of a pressure channel, a temperature channel, or a density channel configured to provide a pressure signal, a temperature signal, and a density signal, respectively, of the fluid sample, wherein the instructions to determine the hydrocarbon composition of the clean fluid comprise instructions executable by the processor to cause the system to determine the hydrocarbon composition of the clean fluid based on at least one of the pressure signal, the temperature signal, or the density signal.

17. The system of claim 13, wherein the memory further has stored thereon instructions executable by the processor to cause the system to determine a reservoir fluid architecture based on the hydrocarbon composition of the clean fluid at multiple locations in a wellbore.

18. The system of claim 13, wherein the memory stores instructions and data that comprise an equation of state, and wherein the processor is configured to execute the equation of state to determine the hydrocarbon composition of the clean fluid based, at least in part, on the first of the measurement fingerprints.

19. The system of claim 13, wherein the multivariate model comprises a linear model or a nonlinear model.

20. A non-transitory, computer readable medium storing instructions which, when executed by a processor, cause a computer to perform operations comprising:

decomposing measurements of a fluid sample into a plurality of contamination levels and a plurality of measurement fingerprints, wherein the measurements were collected across formation depths;

identifying a first subset of the plurality of contamination levels corresponding to a first of the formation depths as contamination levels of mud filtrate at the first depth and a second subset of the plurality of contamination levels corresponding to the first formation depth as contamination levels of clean fluid at the first formation depth; and determining a hydrocarbon composition and a physical property of clean fluid at the first formation depth with a multivariate model based, at least in part, on a first of the measurement fingerprints that corresponds to the first formation depth.

21. The non-transitory, computer readable medium of claim 20, wherein the operations further comprise determining a reservoir fluid architecture based on the hydrocarbon composition of the clean fluid at multiple of the formation depths.

22. The non-transitory, computer readable medium of claim 20, wherein the measurements comprises optical measurements indicative of a spectroscopic characteristic of the hydrocarbon component.

23. The non-transitory, computer-readable medium of claim 20, wherein the measurements comprises at least one of a pressure measurement, a temperature measurement, and a density measurement.

* * * * *